(12) United States Patent
Schlatterer

(10) Patent No.: US 10,864,027 B2
(45) Date of Patent: Dec. 15, 2020

(54) PRE-CONTOURED BUTTRESS PLATE FOR POSTERIOR WALL ACETABULAR FRACTURES

(71) Applicant: Daniel Robert Schlatterer, Dunwoody, GA (US)

(72) Inventor: Daniel Robert Schlatterer, Dunwoody, GA (US)

(\*) Notice: Subject to any disclaimer, the term of this patent is extended or adjusted under 35 U.S.C. 154(b) by 92 days.

(21) Appl. No.: 16/294,023

(22) Filed: Mar. 6, 2019

(65) Prior Publication Data

US 2019/0201063 A1    Jul. 4, 2019

Related U.S. Application Data

(62) Division of application No. 15/298,362, filed on Oct. 20, 2016, now Pat. No. 10,307,192.

(51) Int. Cl.
*A61B 17/80* (2006.01)

(52) U.S. Cl.
CPC .................. *A61B 17/8061* (2013.01)

(58) Field of Classification Search
CPC . A61B 17/80; A61B 17/8052; A61B 17/8057; A61B 17/8061; A61B 17/8066
See application file for complete search history.

(56) References Cited

U.S. PATENT DOCUMENTS

| | | | | |
|---|---|---|---|---|
| 6,440,131 B1* | 8/2002 | Haidukewych | .... | A61B 17/8061 606/286 |
| 9,271,773 B2* | 3/2016 | Hwa | ..................... | A61B 17/809 |
| 9,545,276 B2* | 1/2017 | Buchanan | .......... | A61B 17/8061 |
| 10,307,192 B2* | 6/2019 | Schlatterer | ......... | A61B 17/8061 |
| 2010/0217327 A1* | 8/2010 | Vancelette | ......... | A61B 17/8061 606/281 |
| 2010/0256687 A1* | 10/2010 | Neufeld | ................. | A61B 17/80 606/289 |
| 2011/0137314 A1* | 6/2011 | Kuster | .................... | A61B 17/74 606/70 |
| 2012/0165878 A1* | 6/2012 | Hwa | ..................... | A61B 17/809 606/280 |
| 2012/0226279 A1* | 9/2012 | Lutz | ................... | A61B 17/8066 606/70 |
| 2014/0066996 A1* | 3/2014 | Price | .................. | A61B 17/1728 606/281 |
| 2014/0180343 A1* | 6/2014 | Gaudin | ................. | A61F 2/4225 606/283 |
| 2014/0277176 A1* | 9/2014 | Buchanan | .......... | A61B 17/8014 606/281 |
| 2017/0181784 A1* | 6/2017 | Li | ....................... | A61B 17/1728 |
| 2017/0319249 A1* | 11/2017 | Guo | ..................... | A61B 17/8066 |
| 2018/0110551 A1* | 4/2018 | Schlatterer | ......... | A61B 17/8061 |
| 2019/0201063 A1* | 7/2019 | Schlatterer | ......... | A61B 17/8061 |

\* cited by examiner

*Primary Examiner* — Eric S Gibson
(74) *Attorney, Agent, or Firm* — David L. King

(57) ABSTRACT

An improved posterior acetabular wall fracture buttress plate has a buttress plate having a pair of arms extending from a main plate. The main plate is pre-contoured with a concavity contoured to mimic a hip socket contour posteriorly along an undersurface, the arms being 1.0 cm or less wide and bent lengthwise off horizontal about 38 degrees plus or minus 8 degrees to mimic a curvature of the hip to yield an angle on the undersurface of 142 degrees plus or minus 8 degrees. This is a stand-alone buttress plate intended to accomplish a buttress effect similar to previous art of 2-3 pelvic plates.

12 Claims, 14 Drawing Sheets

PRE-CONTOURED BUTTRESS PLATE FOR POSTERIOR WALL ACETABULAR FRACTURES

RELATED APPLICATIONS

The present invention is a division of U.S. application Ser. No. 15/298,362 filed on Oct. 20, 2016 entitled, "A Pre-Contoured Buttress Plate For Posterior Wall Acetabular Fractures".

TECHNICAL FIELD

The present invention relates to a faster safer and less costly method of stabilizing a fracture of the acetabulum (hip socket).

BACKGROUND OF THE INVENTION

Often bone fractures are reduced surgically and the fracture fragments are immobilized by a metal plate which spans the fracture and has screws going into the plate on either side to secure the fracture fragments while also securing reduction of the fracture so that anatomic healing of the fracture can occur by new bone growth. Ideally, fractures mend in three months or less. In some cases healing takes up to one year. It is therefore essential the repaired fracture stays held securely together for at least the typical three months, if not longer and up to a year.

The metals of plates for fracture are typically stainless steel or other non-corrosive alloy. Attempts to fix posterior wall (PW) acetabular fractures using other commercially available plating systems are limited in two ways 1) These plates must be bent intra-operatively and contoured to fit the curvature of the patient's hip socket, and 2) often multiple plates are utilized to ensure stability to the reduced fracture. The problem with bending the plates during the surgery is that bleeding is ongoing until the incision is sutured closed and the procedure halts and this increases the patient's time under anesthesia which increases the rate of complications such as the need for blood transfusions and adverse reactions to anesthesia. The second problem with the current plating methods is that these methods use multiple plates and screws which increases the cost of the orthopaedic procedure to the patient, and the use of multiple plates is time consuming and this increases complication rates for the patient as noted above. The present invention provides faster and better stabilization of a posterior wall acetabular hip socket fracture by way of reducing fixation to a single plate and eliminating the need for intra-operative plate bending to fit the hip socket anatomy.

In bone surgeries, such as for fixation (i.e., fusion and unification of fractured bones) of reduced and realigned bones after a displaced bone fracture, the bones, in order for their mending and healing to occur, must be reduced and be kept held tightly together, so that they may not be dislocated or re-displaced before their fusion is complete. For this holding, steel plates have long been used, along with, depending on the situation, a variety of devices such as metal, plates, rods, hooks, bolts (pedicle screws) and the like. Recently an advancement in metal plate design produced an option for the metal bone screws to screw into the plate as well as the bone these newer plates are referred to as locking plates. This invention presented herein incorporates locking screw concepts with the added features of being pre-contoured to fit the hip socket curvature and the ability to buttress a fracture in this region with a single plate as opposed to using 2 or 3 plates. This invention presented herein incorporates limited contact plating concepts with the added features of being pre-contoured to fit the hip socket curvature without the need for further manipulation in the operating room (OR) and the ability to buttress a fracture in this region with a single plate as opposed to using 2 or 3 plates.

It is therefore an objective of the present invention to provide a bone binding construct capable of securing the hip socket posterior wall (PW) bone fracture while avoiding or greatly minimizing the operative time and expense of current fixation methods.

SUMMARY OF THE INVENTION

An improved bone plating for posterior hip socket fractures has locking screw capability for the posterior wall fragment, these locking screws which are directed and angled in such a way so as to avoid intra-articular placement. The hip socket has a defined concavity matching the size and shape of the femoral head. The posterior wall fragment locking screws of this invention are intended to avoid penetration of the femoral head and the hip joint. The length of screws to be placed in this region will vary and will be at the discretion of the surgeon. It is further conceived that an assortment of these pre-contoured plates will be made available in various lengths and widths to fit the myriad of posterior wall fracture patterns. The invention provides a method of immobilizing a posterior wall fracture or osteotomy or hardware for any and all hip socket reconstructive procedures and so forth having the steps of surgically isolating the region of the bone to be immobilized, binding the bone with a length of plating having discontinuous points of contact. Most metal plate designs for fractures incorporate scallops on the under surface of the plate for the purpose of limited plate contact to the bone as the plate is fixed to the bone with bone screws. The limited contact plate feature with undersurface scallops is preferably utilized in this new invention to allow for additional minor plate bending if required. The difference again in this plate is that it is pre-contoured and can achieve the same result as a combination of 2-3 plates with less risk of operative complications to the patient and less expense to the patient as well.

In one preferred embodiment, improved stand-alone bone plating implant or stand-alone buttress plate for Posterior Wall (PW) hip socket fractures has seven 2.8 mm locking screw options or holes for capturing the posterior wall fragment. These 7 screw options are directed medially towards the posterior column of the pelvis and angled in such a way so as to avoid intra-articular hip joint positioning or femoral head placement. The length of locking screws to be placed in this region will vary and would be at the discretion of the surgeon. The remainder of this buttress plate overlying the Posterior Wall and posterior column (PC) has the capability for 4-6 3.5 mm locking or non-locking screws (see FIGS. 11A and 11B). The hip socket has a defined concavity matching the size and shape of the femoral head. The length of all locking and non-locking screws to be placed in this buttress plate will vary and would be at the discretion of the treating surgeon. It is further conceived that an assortment of these pre-contoured buttress plates would be made available in a set of various lengths and widths to fit the myriad of posterior wall fracture patterns and to fit the slight differences in adult and pediatric anatomic dimensions. The present invention provides a method of immobilizing a posterior wall fracture or osteotomy or hardware for any and all hip socket reconstructive procedures and so forth having the steps of isolating the region of the bone to be immobilized, binding the bone with a length of plating having discontinuous points of limited bony contact, Most current plates designed for fractures incorporate scallops on the under surface of the plate for the purpose of reducing the area of contact between the plate and the bone it is fixed to with bone screws this plate continues that convention, This limited contact plate feature is preferably utilized in the preferred present invention to allow for additional minor plate bending if required. The difference again in this buttress plate is that it is pre-contoured to fit hip socket anatomy without the need for further manipulation in the OR and can achieve the same fracture buttressing effect that would result from a combination of a more expensive 2-3 plate construct. Furthermore, this is the first limited contact plate designed specifically in this shape with limited contact properties and the capacity for locking screws for repair of a PW fracture. This plate is designed and intended to be positioned over a fracture of the acetabular posterior wall and/or posterior column with the pre-contoured portion of the buttress plate juxtaposed to the hip socket margin posteriorly. Surgeons of fracture repair may find indications and application for this buttress plate elsewhere in the axial and appendicular skeleton. This is a stand-alone plate intended and designed to replace the typical 2 and 3 plate constructs used currently for these complex posterior acetabular fracture patterns. This buttress plate envisions several 0.5-1.0 mm additional smooth holes 53 (FIG. 11A) interposed in and around the (7) 2.8 mm locking holes 50 these holes 53 would be for suture passage and hip capsular repair. These holes 53 are not found on the prototype plate in FIG. 11B

BRIEF DESCRIPTION OF THE IMAGES

The invention will be described by way of example and with reference to the accompanying drawings in which.

Figure 1:
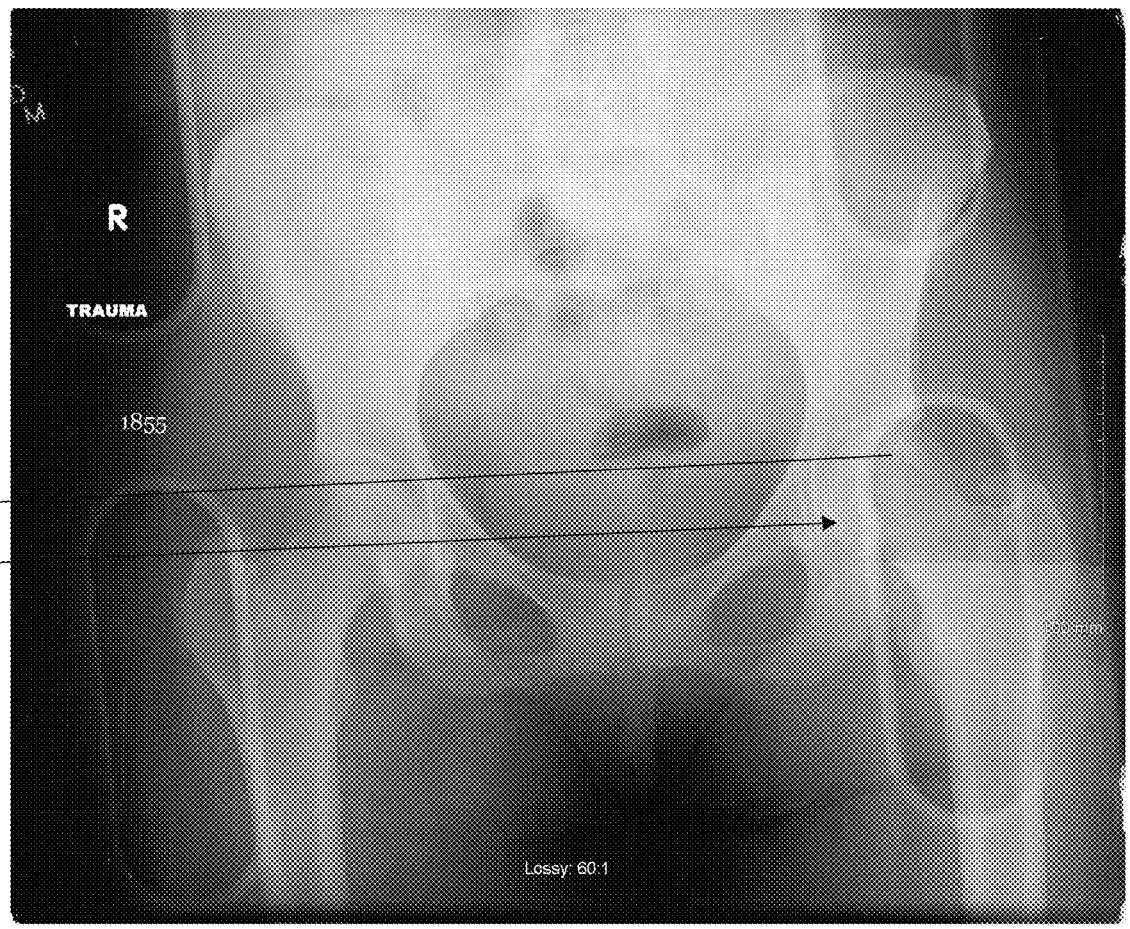
FIG. 1 is an exemplary x-ray of a patient exhibiting a left hip socket fracture.
Figure 2:
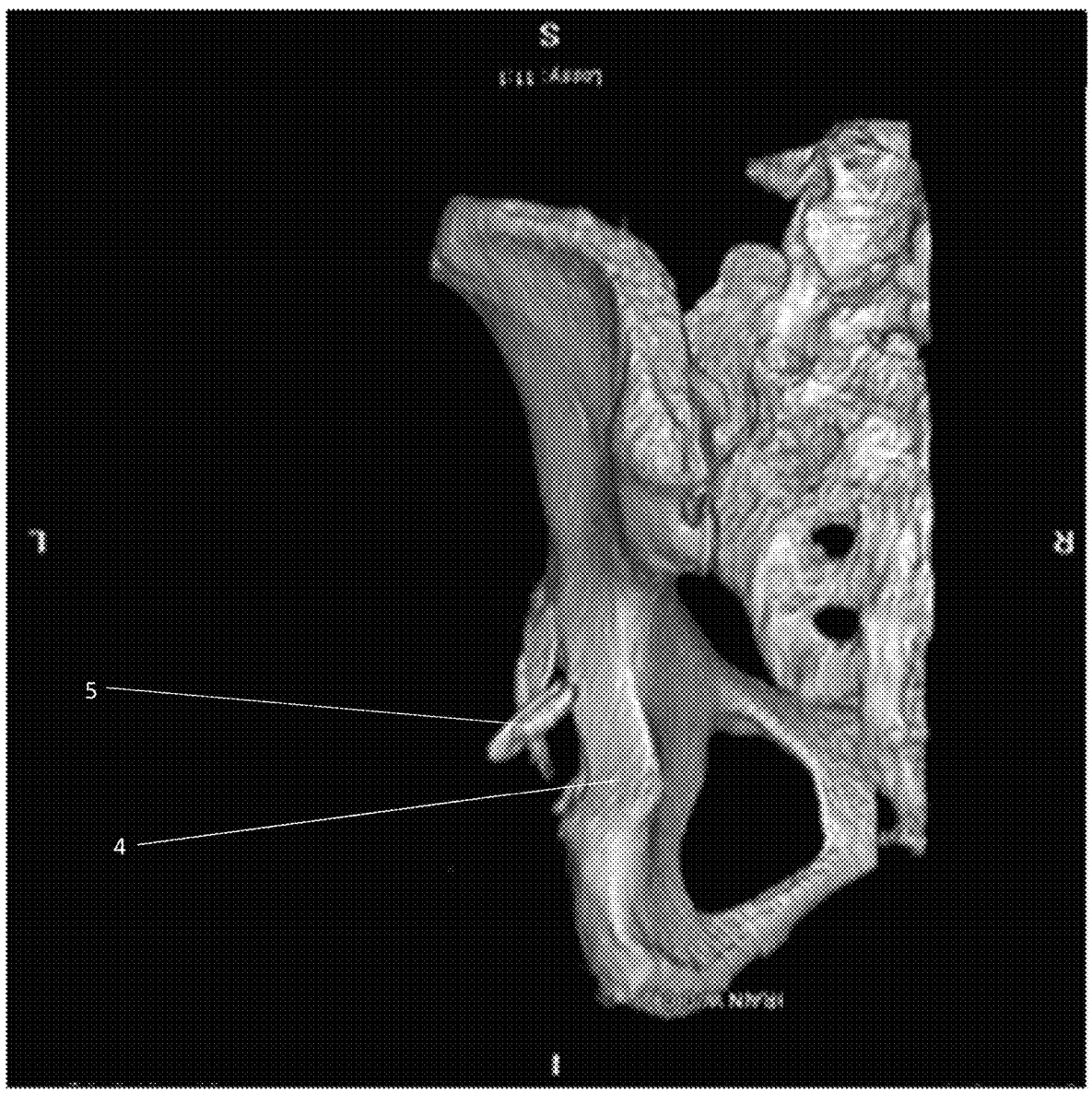
FIG. 2 is a first 3D CT scan of the hip of the patient of FIG. 1.
Figure 3:
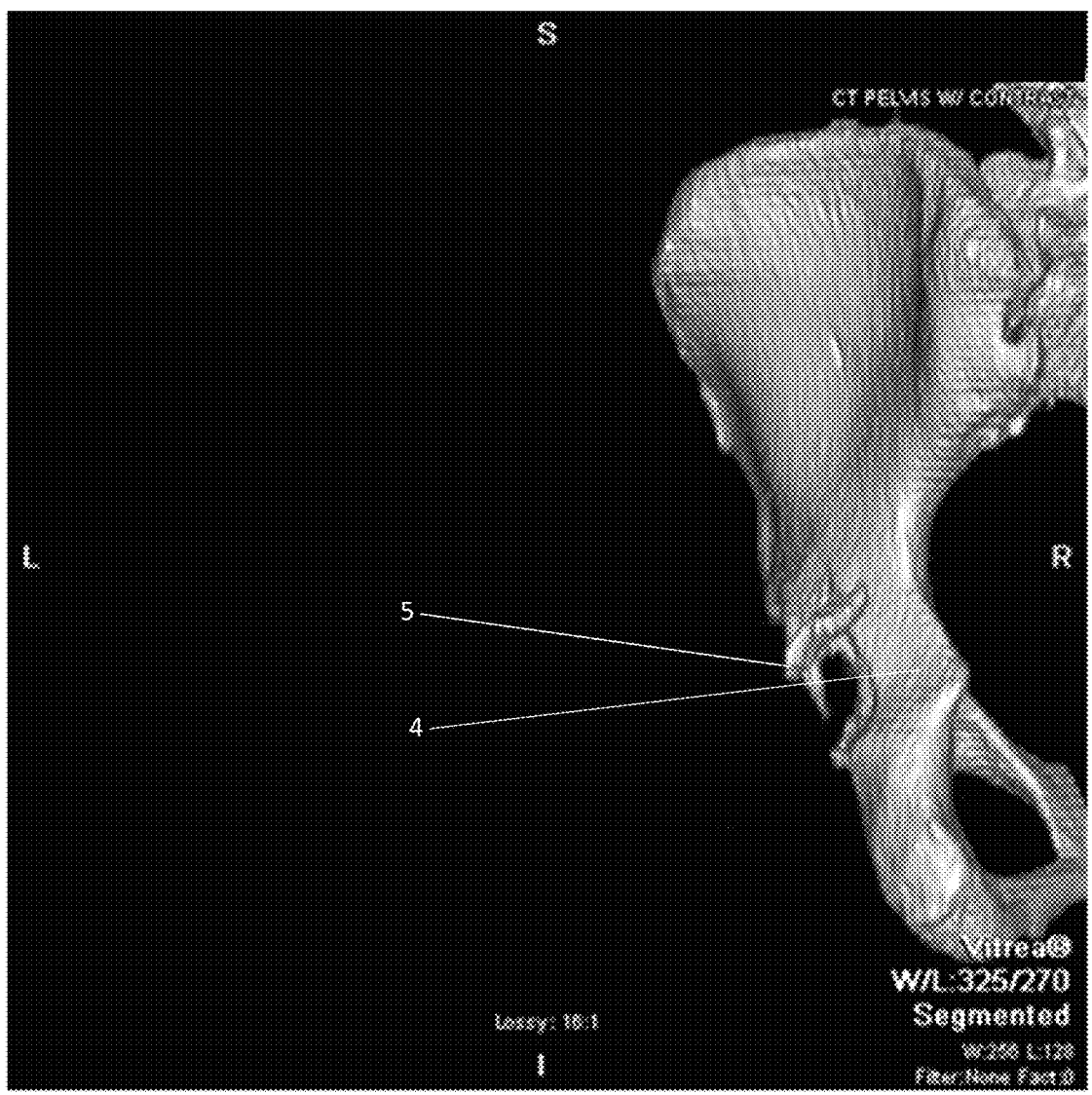
Figure 4:
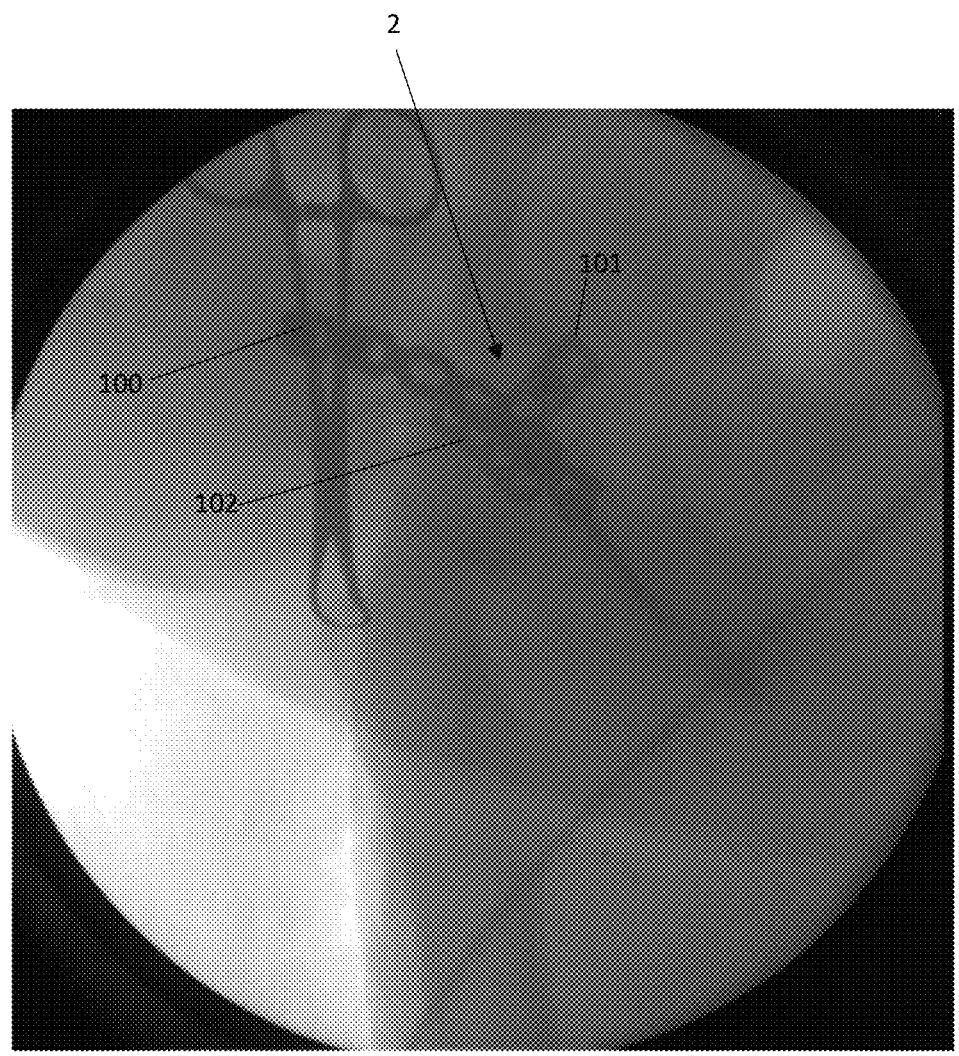

FIG. 3 is a second 3D CT scan of the hip of the patient of FIG. 1. Note how small the two fracture fragments are. Their small size makes screw fixation challenging FIG. 4 is an x-ray of an expensive multiple plate stabilization construct of the patient of FIGS. 1, 2 and 3.

Figure 5:
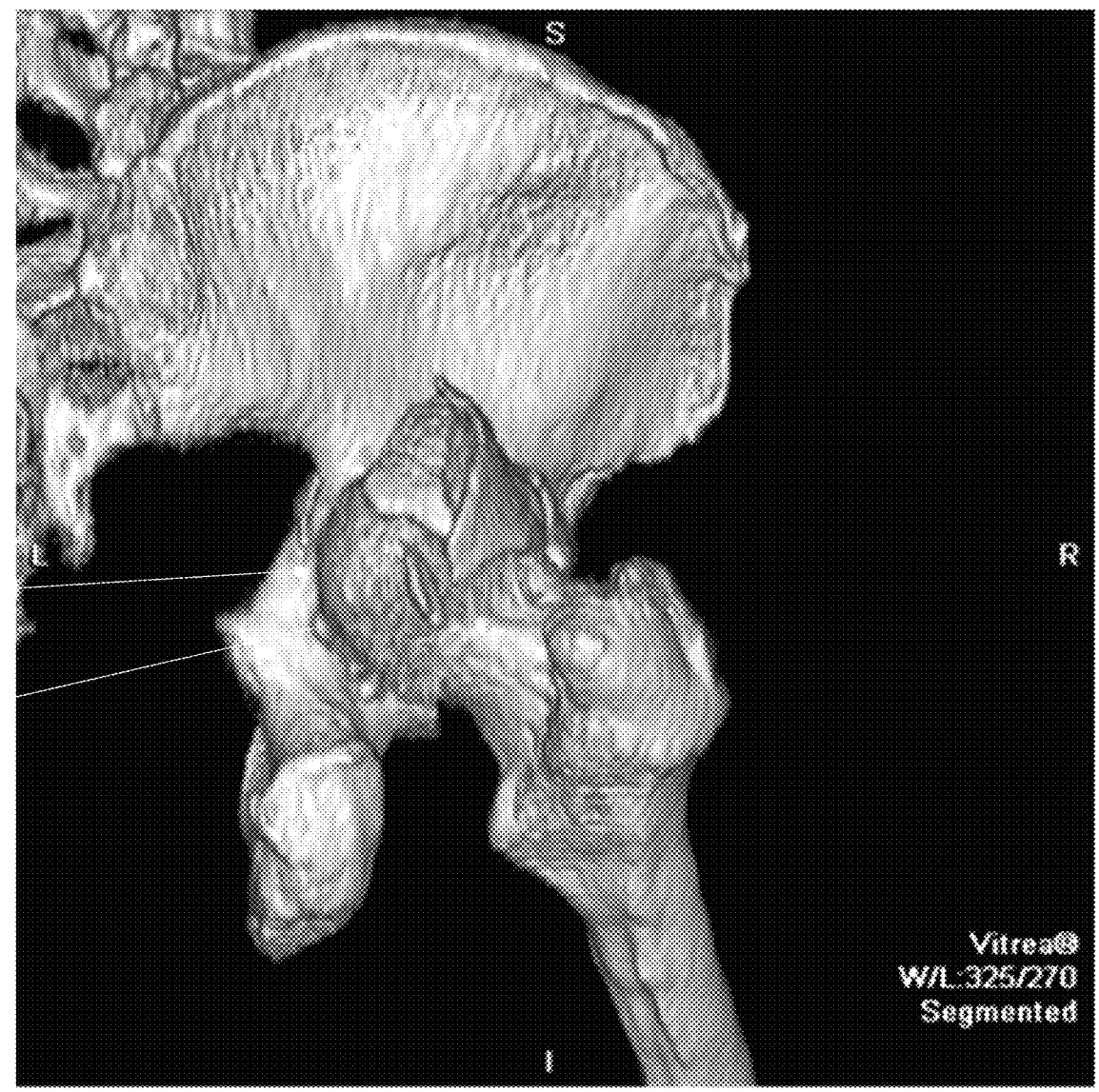

FIG. 5 is a 3D CT scan of a second patient exhibiting a hip fracture with larger fracture fragments which leads to the need for a plate buttress construct with larger surface area coverage such as the present invention or the use of multiple plates.

Figure 6:
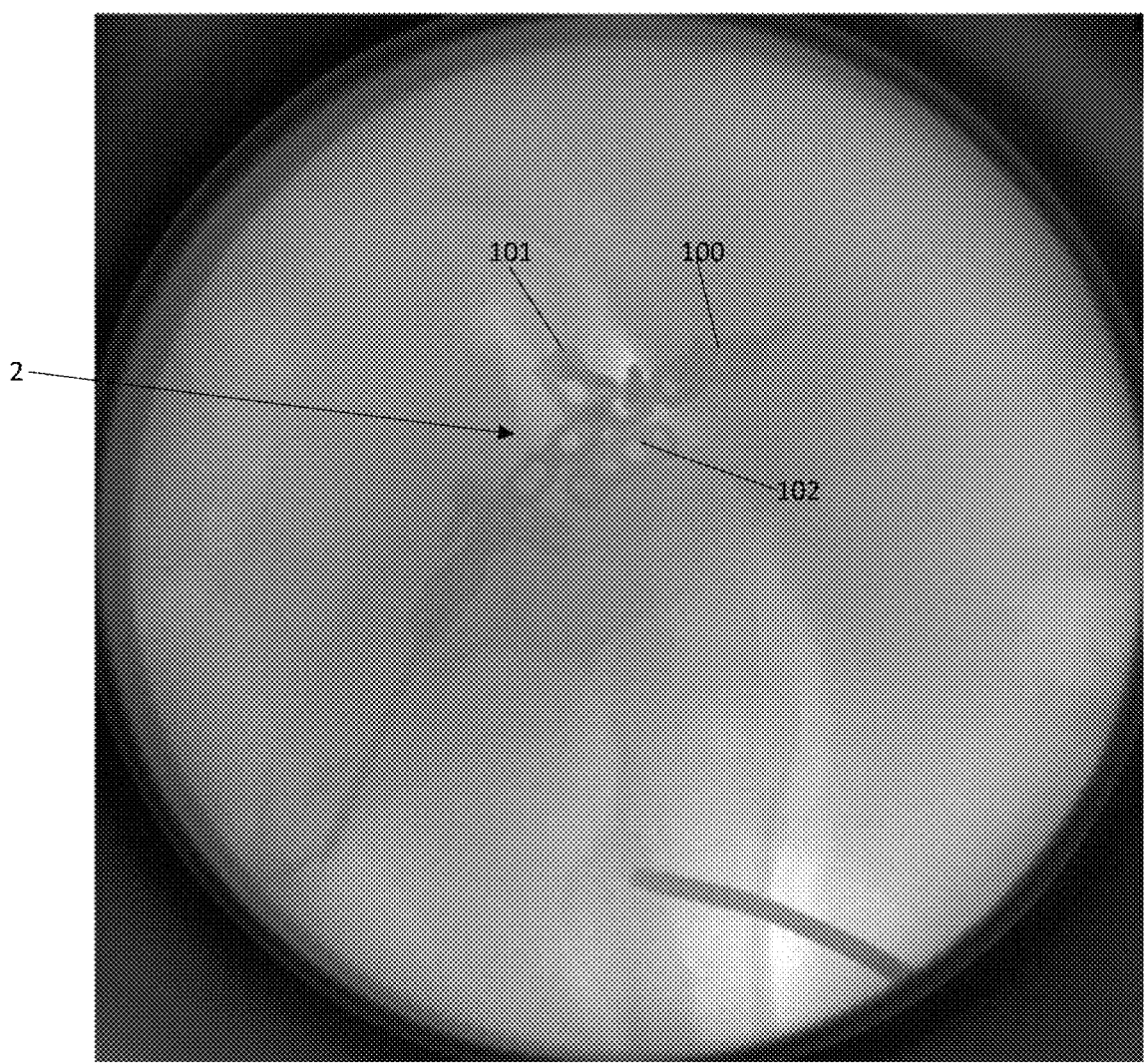

FIG. 6 is an intra-operative x-ray of the second patient with multiple plates in place.

Figure 7:
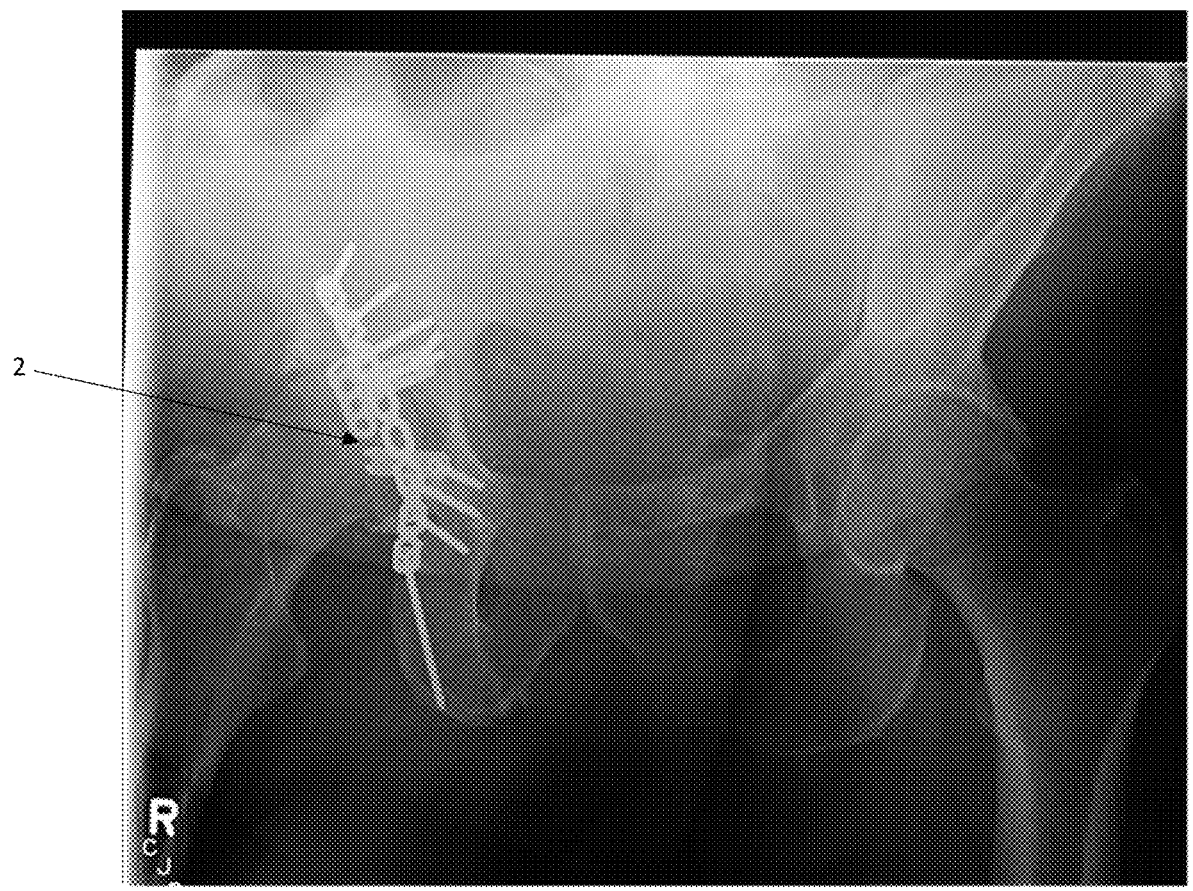

FIG. 7 is a post-operative second x-ray of the second patient with multiple plates in place.

Figure 8:
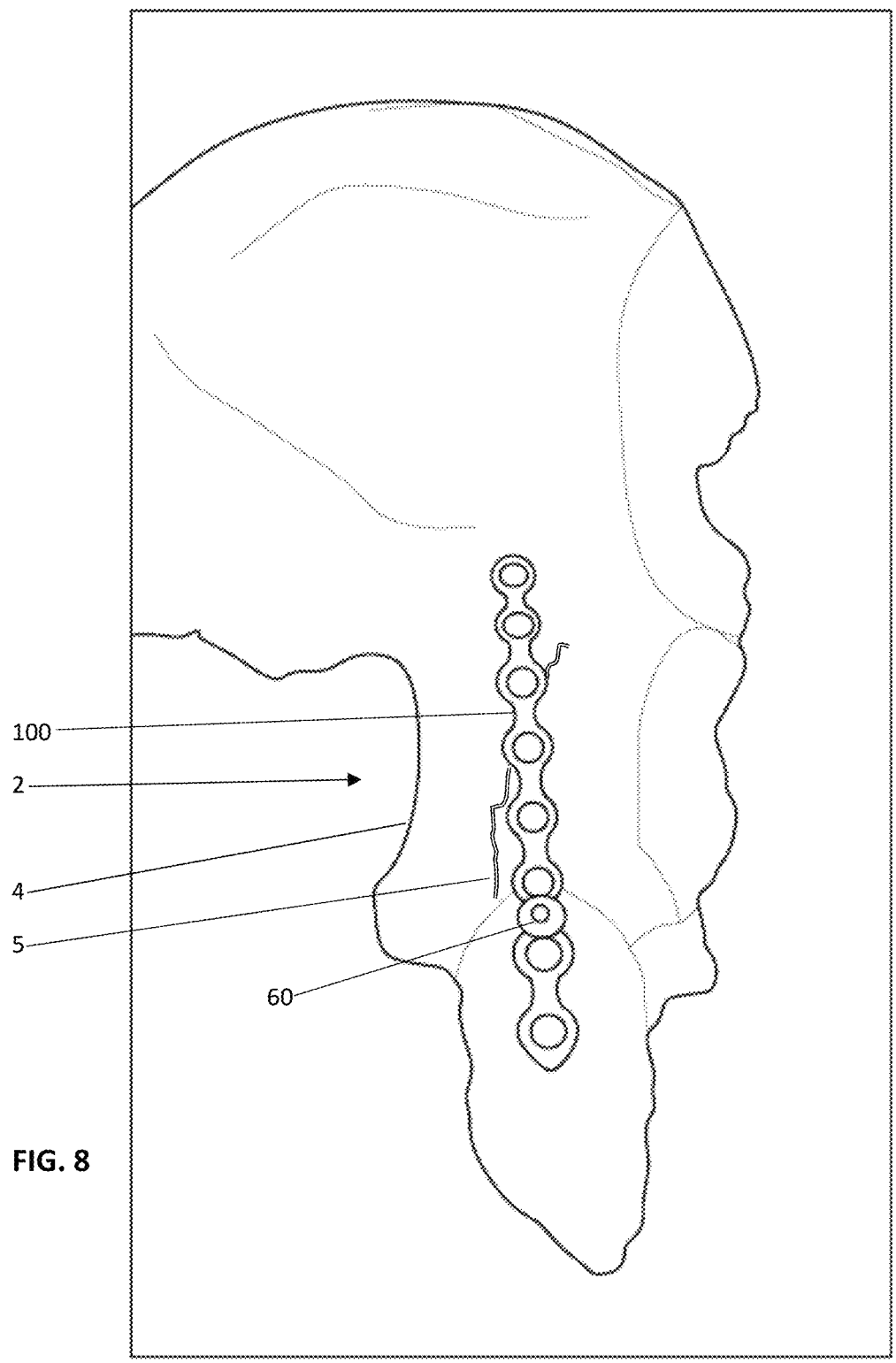

FIG. 8 is a line drawing of a conventional prior art hip fracture repair.

Figure 9:
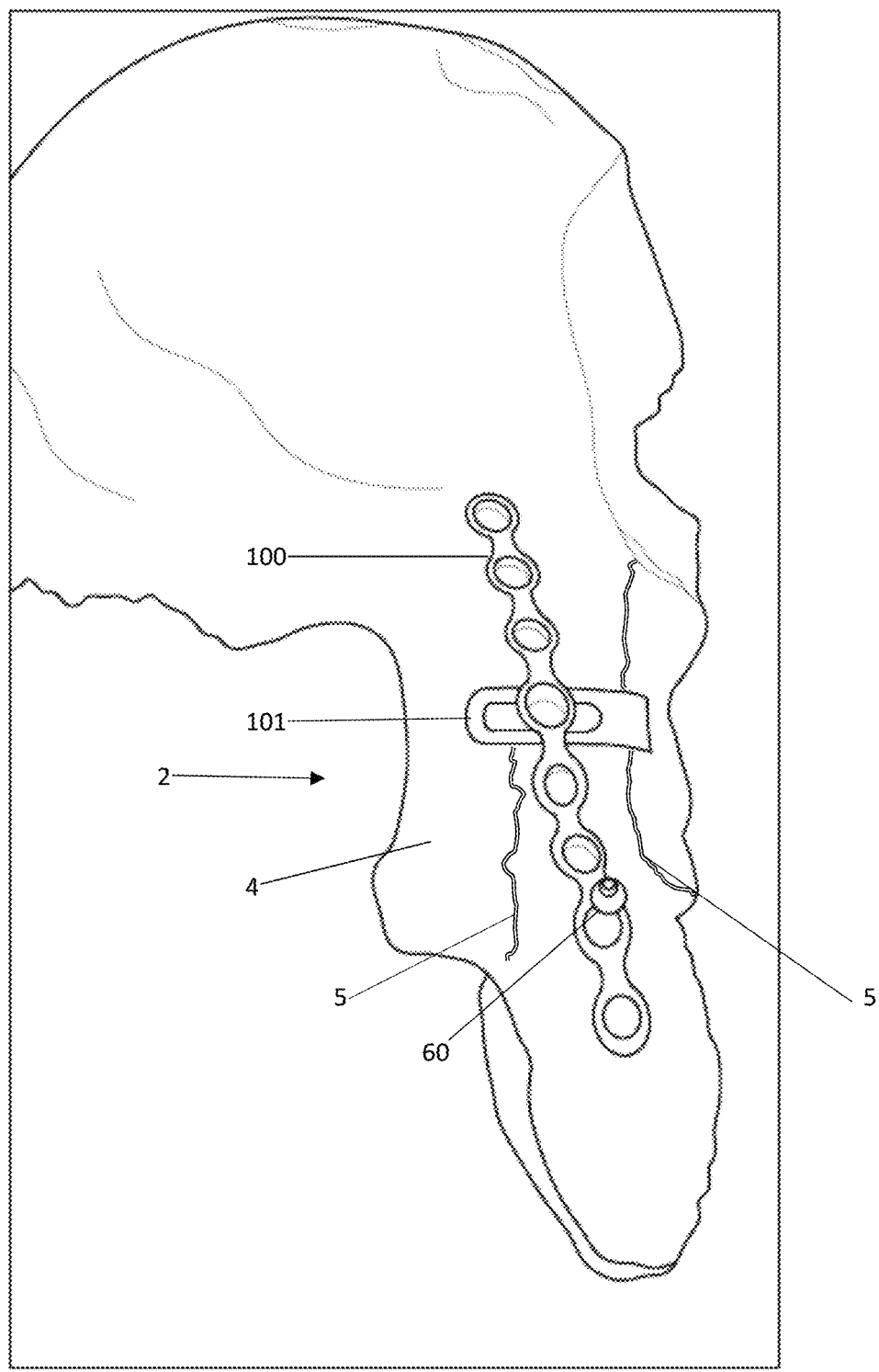

FIG. 9 is a line drawing of a conventional prior art hip fracture repair with two plates.

Figure 10:
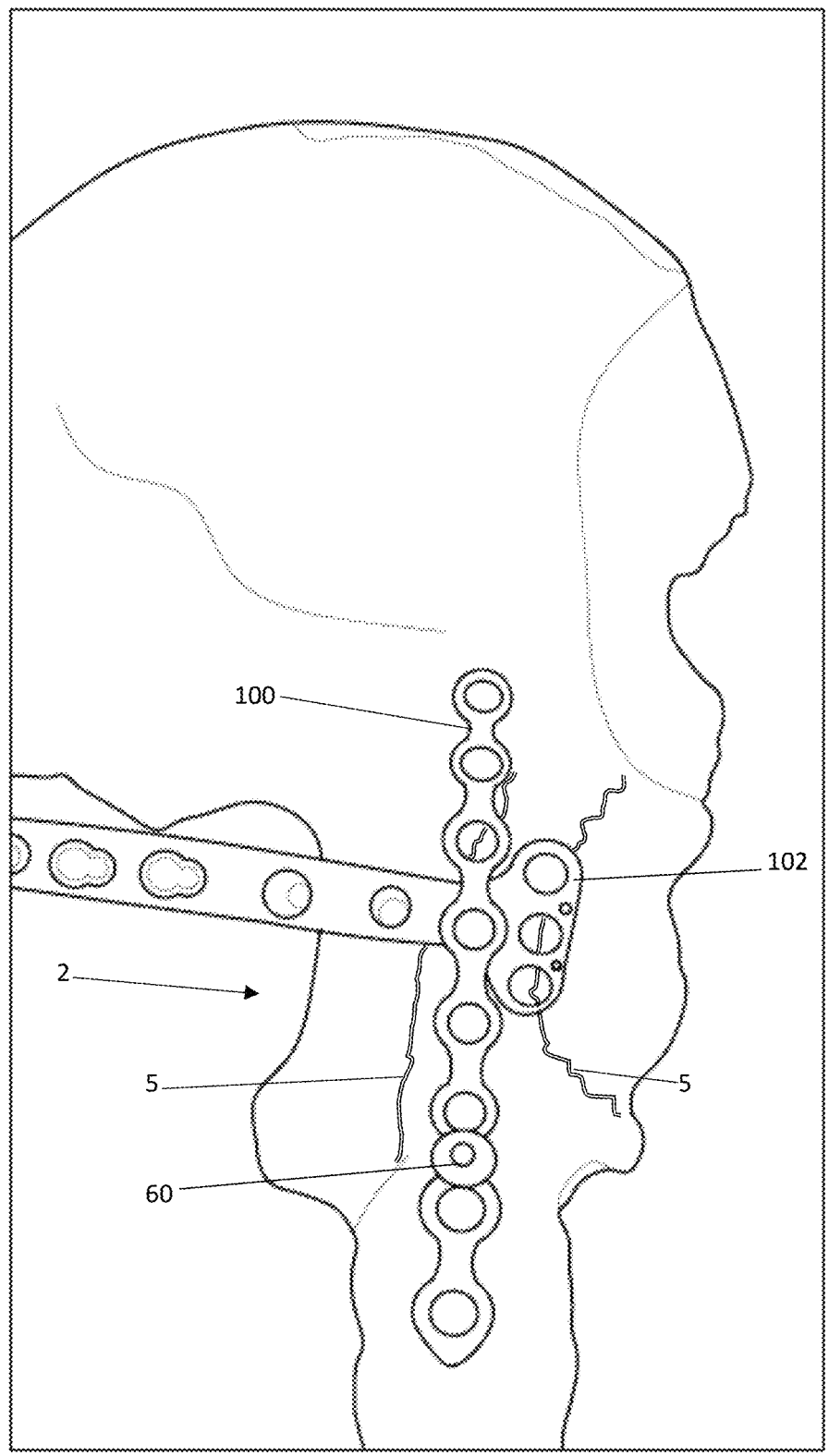

FIG. 10 is a line drawing of a conventional prior art hip fracture repair with a "T" plate underlying a long narrow pelvic reconstruction plate.

Figure 11A:
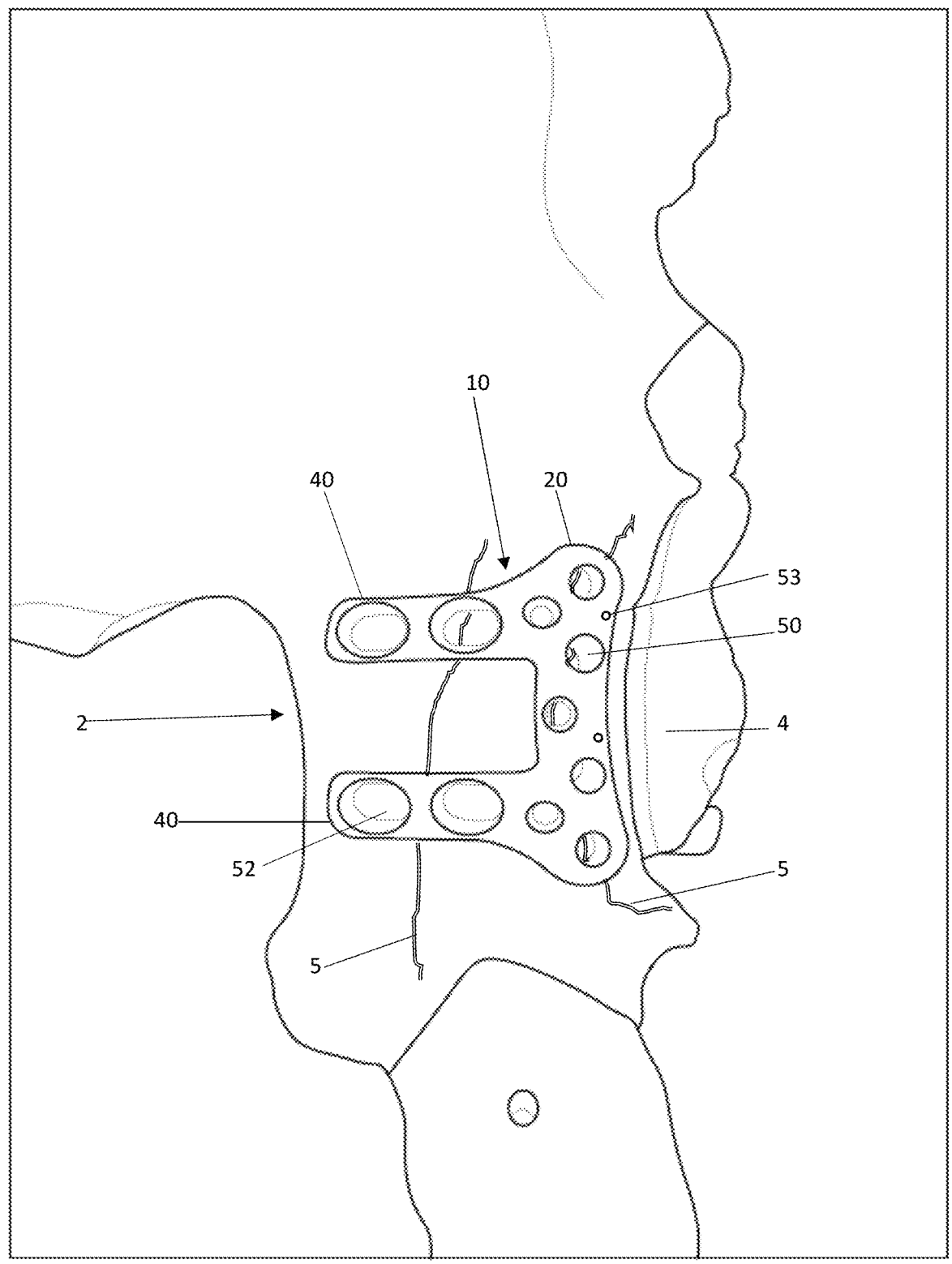

FIG. 11A is a line drawing of a hip fracture repair utilizing the pre-contoured plate of the present invention.

Figure 11B:
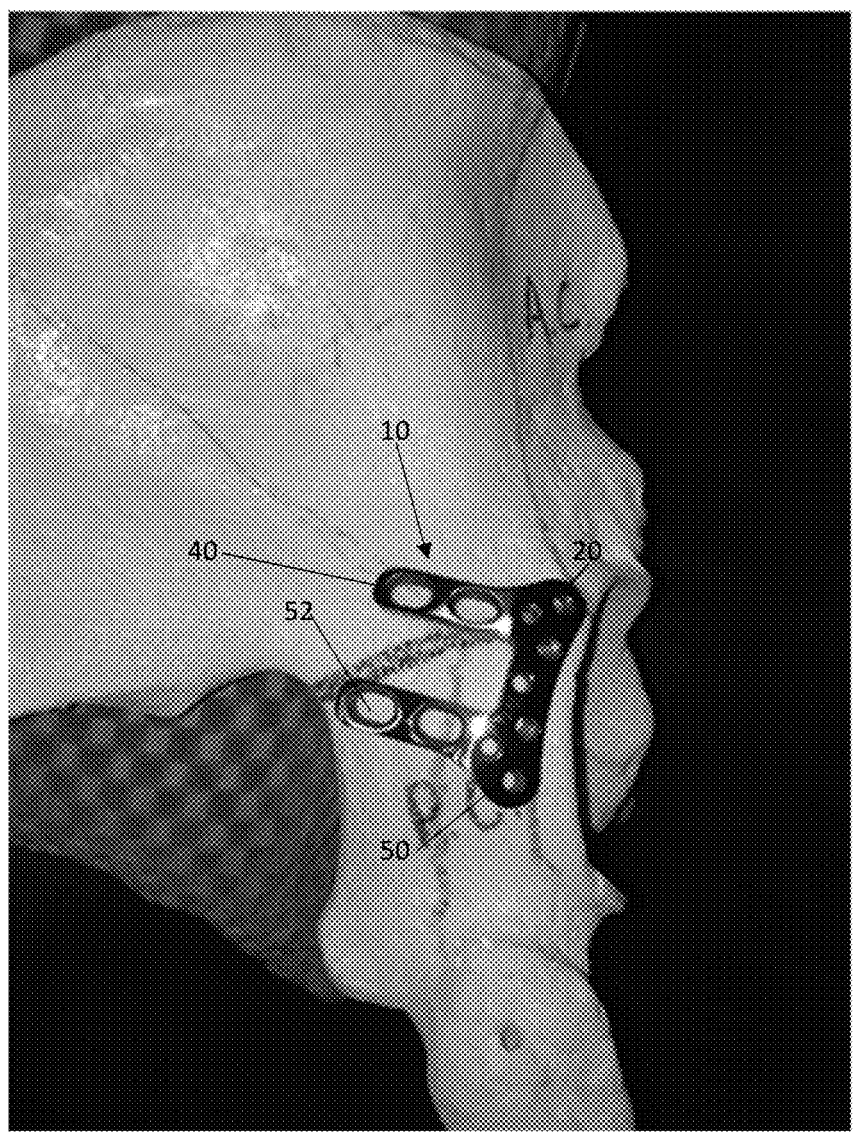
Figure 12A:
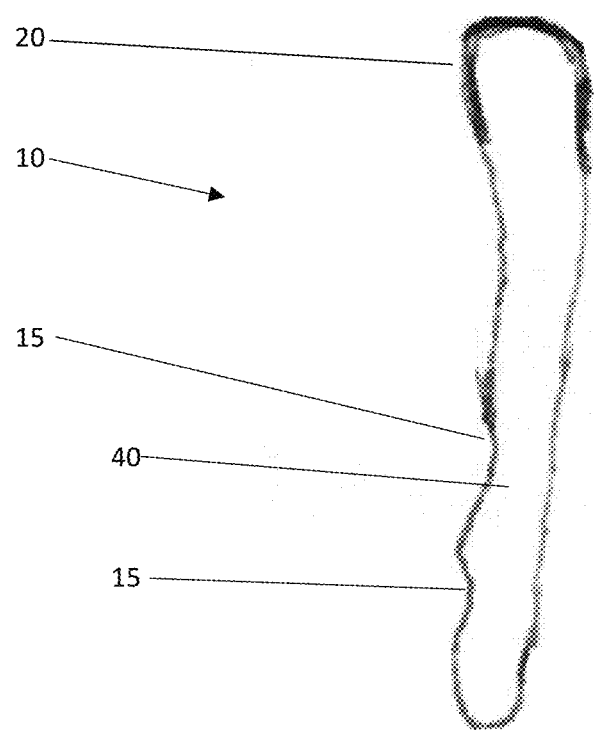

FIG. 11B shows the plate rotated to accommodate a different preferred stabilization. This figure show a prototype in place on a plastic saw bone pelvis model FIG. 12A is a side plane view of the plate of the present invention.

Figure 12B:
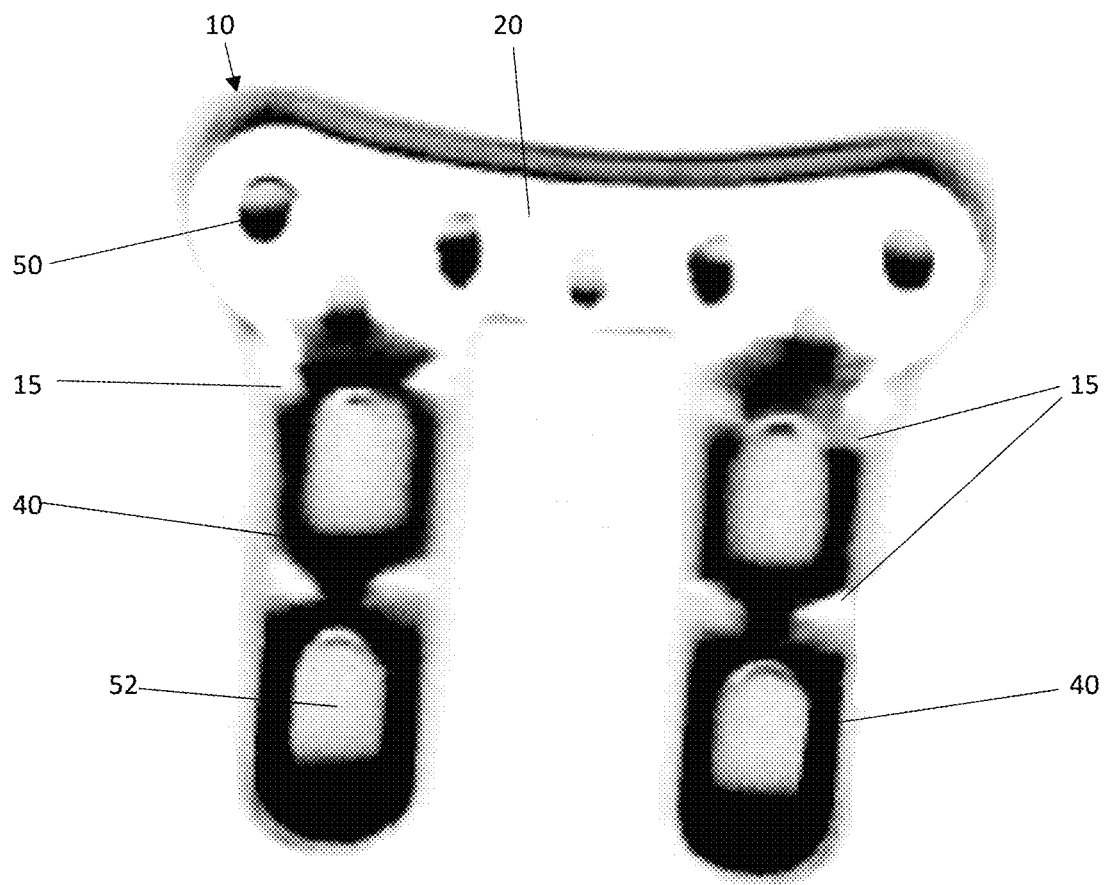

FIG. 12B is a plan underside perspective view of the plate of the present invention.

DETAILED DESCRIPTION OF THE INVENTION

A stand-alone pre-contoured buttress plate 10 with the capacity for (5-7) 2.8 mm locking screws 60 nearest the Posterior Wall fragment (4-6) 3.5 mm locking or non-locking screws 60 in the main plate segment 20 overlying the pelvic posterior column. It is further conceived that an assortment of these pre-contoured buttress plates 10 would be made available as a kit in a set of various lengths and widths to fit the myriad of posterior wall 4 fracture patterns 5 and to fit the slight differences in adult and pediatric anatomic dimensions. One version of this plate 10 envisions 0.5-1.0 mm additional smooth holes interposed in and around the (7) 2.8 mm locking holes 50 these holes would be for suture passage and hip capsular repair (FIG. 11A). The buttress plates of the present invention are made of an implantable metal such as surgical grade stainless steel.

With reference to FIGS. 1-7, various views taken by x-ray or CT scans show an exemplary fractured hip 2 of a patient.

FIG. 1 is an anterior-posterior (AP) radiograph of a pelvis the patient's fractured left hip socket is to the viewer's right hand side and the right non-injured hip is to the viewer's left hand side vice versa. In the upper and outer right hand corner of the left hip 2 a white density can be seen this is a bone fragment representing a posterior wall 4 fracture 5.

FIG. 2 is a 3D reconstruction of a CT scan of the patient in FIG. 1. Note the narrowness of fracture 5 fragments. FIG. 3 is a complimentary image to FIG. 2. It is also a 3D reconstruction of a CT scan of the patient in FIG. 1. Note how narrow the fracture 5 fragment is. Small fragments are a challenge to hold securely for months during the healing process after reduction. Compare and contrast this fracture pattern to the fracture pattern in FIG. 5 of a different patient.

FIG. 4 is an intra-operative fluoroscopic image demonstrating 3 plates 100, 101, 102 forming a construct to stabilize a Posterior Wall 4 fracture according to the current prior art practice. This multi-plate construct has the smaller plates placed right up to the edge of the hip 2 socket with another longer plate bent and placed over each smaller plate to reinforce and buttress the PW fracture 5. There is a clamp in this image with no purpose in the fracture repair process.

With reference to FIG. 5, a different patient with larger and wider fractures is shown in a view similar to images of FIGS. 2 and 3. This is also a 3D reconstruction of a CT scan but of the different patient than the patient depicted in FIG. 1. It is noted how much larger and different the fracture fragments are in this image. This fracture pattern would require multiple plates for stabilization according to the current prior art practice which adds time and cost to the procedure or preferably at a much lower cost in time and quality of stabilization as will be discussed; or one broader plate 10 made in accordance with the present invention to stabilize all 3 fragments simultaneously.

FIG. 6 is similar to the image of FIG. 4. This is also an intra-operative fluoroscopic image demonstrating 3 plates forming a construct to stabilize the Posterior Wall 4 fracture depicted in FIG. 5. FIG. 7 is somewhat similar to images of FIGS. 4 and 6. This is a post-operative AP radiograph demonstrating 3 plates 100, 101, 102 forming a wide construct to stabilize a complex Posterior Wall 4 fracture such as seen in FIG. 5.

See images of FIGS. 9 and 10 for further illustration of this multi-plate construct where the smaller plates 101 are placed right up to the edge of the hip 2 socket with the longer plate 100 being contoured by being bent and placed over each to hold these plates 101, 102 in place. Collectively the three plates 100, 101, 102 are buttressing this complex fracture 5 pattern.

FIG. 8 is a representation of a plastic model of a pelvis including a hip 2 socket. The model is positioned such that the back of the right hip 2 socket bone stock is easily visualized. The vertical double lines 5 represent typical posterior wall fracture lines 5 analogous to the thin fracture fragments seen in FIG. 1 and the CT scan of FIGS. 2 and 3. The fracture length is approximately 60 mm in length. An 8 hole stainless steel metal pelvic reconstruction plate 100 is just to the left of the fracture lines 5. This plate 100 is bendable and may receive screws 60 in 8 various locations. All of the bone to the right of the plate is considered the posterior wall (PW) of the acetabulum. All of the bone under and to the left of this plate 100 is considered the posterior column of the pelvis. Note the letters "P" and "C" marking this posterior column area. This 8 hole plate is also seen in FIGS. 6, 7, 9, and 10. The long plate in FIG. 4 is very similar except it is a 6 hole pelvic reconstruction plate.

FIG. 9 is nearly identical to the previous FIG. 8 except now there is a thin 2 hole plate 101 under the 8 hole plate 100. This second plate 101 is crossing the double "fracture" line 5 and is very close to the margin of the hip 2 socket. This second plate 101 is approximately 20 mm in width. As can be seen in this schematic, the second smaller plate 101 covers only a small percent roughly 30% of the entire fracture length. This 2 plate construct is depicted radiographically in images of FIGS. 6 and 7. Collectively, these two plates 100, 101 could buttress a potentially complex fracture pattern, as shown in the CT scan in FIG. 5.

The FIG. 10 image is nearly identical to the previous FIGS. 8 and 9, except now there is a multi-holed "T" shaped plate 102 under this 8 hole plate 100. This second plate 102 is crossing the double "fracture" line 5 and is very close to the margin of the hip 2 socket. This second plate 102 is approximately 30 mm in width at the "T" portion of the plate. As can be seen in this schematic the second smaller plate 102 covers only a small percent roughly 50% of the entire fracture length which is more than the 2 hole plate 101 covered in the previous FIG. 9. This common 2-plate construct is depicted radiographically in FIGS. 6 and 7. Collectively, these two plates 100, 102 could buttress a potentially complex fracture pattern, see CT scan in FIG. 5. The "T" plate 102 is a distal radius plate not designed nor indicated for acetabular fractures and carries a significant added cost to the patient.

All of the above current prior art solutions are complex and very tedious to shape and secure for a proper stabilization of the posterior wall PW fracture. FIG. 11A is the same model of a pelvis including a hip 2 socket. The model is positioned such that the back of the right hip socket bone stock is easily visualized. The vertical double lines 5 represent typical posterior wall fracture lines 5 analogous to the thin fracture fragments seen in figure 1 and the CT scan of FIG. 4. This plate invention is overlying the Posterior Wall fracture similar to the multi-plates shown in FIGS. 8, 9 and 10, except now the fracture is covered by a plate 10 for nearly 100% of its length, compare and contrast with FIGS. 9 and 10. Also note there are 7 options or holes 50 for 2.8 mm locking screws all angled sufficiently away from potential trajectory into the hip socket. The four remaining and larger holes 52 in the plate overlying the posterior column could be machined to accommodate 3.5 mm locking or non-locking screws 60, or a combination thereof.

FIG. 11B is somewhat similar to a plane side view of the plate of FIG. 11A. The purpose of this image is to illustrate how, due to its pre-contoured shape, easily this plate 10 could be rotated to fit over and buttress a different PW fracture 5 pattern. The plate curvature follows the hip 2 socket curvature even as it is rotated away due to the pre-contoured angularity being about 38 degrees.

As shown in FIGS. 11A and 11B, the buttress plate 10 has a main plate 20 with two arms 40 extending generally perpendicular to the length of the main plate 20. As shown, the overall length of the main plate 20 is less than 4 cm, preferably about 3.8 cm. As shown, it has 7 holes 50 positioned therethrough to receive 2.7 mm or 2.8 mm locking screws 60. The holes 50, when formed as locking holes, have threads or are threaded. The arms 40 are less than 1 cm wide, preferably 0.8 cm, and about 3 cm long or longer with 2 or more holes 52 for receiving 3.5 mm cortical screws. The buttress plate 10 is configured for stabilizing posterior wall 4 acetabular fractures 5.

In FIG. 12A, a side profile shows the contoured cavity of the main plate 20 has a curvature mimicking the surface contour of the hip 2, preferably at a radius of bend slightly larger than the arc of the hip bone. This sizing allows the plate 10 to pivot angularly to accommodate a variety of fracture patterns and their inclined metal plate construct stabilization positions.

As shown in FIG. 12B, the underside has scallops or ridges or projections 15 to insure limited surface contact to the bone and to facilitate modest bending if slight adjustments are needed. Ideally, the curvature of the main plate 20 forms a 38 degree bend off horizontal, accordingly, a flat plate is 180 degrees while the preferred main plate 20 is bisected along a midline bent to 142 degrees, while the arms 40 extend along the bend at the same inclination. This allows the buttress plate 10 to be positioned along a wide range of inclinations while still mimicking the posterior wall 4 curvature. The thickness of the plate 10 is 3 mm or less allowing the arms 40 to flex against the bone during fixation.

It is understood the plates 10 can be provided in a kit having a range of arm 40 lengths, preferably in 1 cm increments up to 10 cm and the number of holes 52 increased from 2 holes for 3 cm, up to 6 or 8 holes depending on the length of the arm 40. Similarly, the kit of buttress plates 10 could have the main plate 20 be longer than 4 cm and wider than 1.5 cm. Each plate increases in increments of 0.5 cm allowing for up to 8 cm in length and 3 cm in width, if so desired. Also, the kit can provide the bend of 38 degrees off horizontal yielding 142 degree inclination to be increased to a bend of 45 degrees or 135 degrees inclination for smaller patients and decreased to 30 degrees or 150 degrees inclination for larger patients. As such, the surgeon can select the optimum size for the patient and suitable to stabilize the fracture lines.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

The invention claimed is:

1. A method of immobilizing a bone comprising the steps of:
   isolating a region of bone to be immobilized;
   reduction and temporary fixation of a plurality of fracture fragments with wires or reduction clamps;
   anatomic positioning of a buttress plate in a best buttress position;
   drilling and measurement steps for selected screw placement;
   removal of provisional fixation devices including wires and clamps;
   intra-operative fluoroscopic imaging to confirm fracture reduction and suitable buttress plate positioning; and fixation of screws.

2. The method of claim 1 further comprising the step of:
   stabilizing the bone in any and all situations of bone instability including, but not limited to situations of fracture, osteotomy, non-union and need or use for the bone binding including, but not limited to, an inclusion of metal plates or other hardware devices to achieve bone stabilization.

3. The method of claim 1 further comprises the step of:
   utilizing one or more metal plates or other hardware devices to stabilize the bone as indicated between different fracture patterns.

4. The method of claim 3 further comprises the step of:
   attaching a bone binding to the one or more metal plates or other hardware as indicated between different fracture patterns.

5. The method of claim 1 wherein the step of positioning the buttress plate in the best buttress position includes the buttress plate having a pair of arms extending from a main plate, the main plate being pre-contoured with a concavity contoured to mimic a hip socket contour posteriorly along an undersurface.

6. The method of claim 5 wherein the arms are 1.0 cm or less wide and bent lengthwise off horizontal relative to the main plate 38 degrees plus or minus 8 degrees to mimic a curvature of a hip to yield an angle on the undersurface of 142 degrees plus or minus 8 degrees.

7. The method of claim 6 wherein the main plate of the buttress plate has at least seven locking screw options or holes for positional fixation of a posterior wall fracture fragment.

8. The method of claim 7 wherein the buttress plate is configured to buttress and inclined and angularly positioned relative to the hip contour to support a fracture surface area by having the contoured main portion sized to allow rotation of the buttress plate.

9. The method of claim 8 wherein the undersurface of the buttress plate has scallops or ridges or protrusions to provide limited bone contact.

10. A kit of buttress plates comprises:
    a plurality of buttress plates, each buttress plate having a main plate;
    wherein the kit has at least one smaller buttress plate with a small contoured curvature for smaller patients and at least one larger buttress plate with a larger contoured curvature for larger patients, the kit including one or more buttress plates having a pair of arms extending from the main plate, the main plate being pre-contoured with a concavity contoured to mimic a hip socket contour posteriorly along an undersurface bent lengthwise off horizontal relative to the main plate at 38 degrees plus or minus 8 degrees to mimic a curvature of the hip to yield an angle on the undersurface of 142 degrees plus or minus 8 degrees, the arms being 1.0 cm or less wide.

11. The kit of claim 10 wherein the larger buttress plate has a bend angle of 30 degrees off horizontal relative to the main plate yielding an angle of 150 degrees.

12. The kit of claim 10 wherein the smaller buttress plate has a bend angle of 45 degrees off horizontal relative to the main plate yielding an angle of 135 degrees.

\* \* \* \* \*